United States Patent
O'Donnell, Jr.

[11] Patent Number: 5,507,740
[45] Date of Patent: Apr. 16, 1996

[54] CORNEAL TOPOGRAPHY ENHANCEMENT DEVICE

[76] Inventor: Francis E. O'Donnell, Jr., 709 The Hamptons, Chesterfield, Mo. 63017

[21] Appl. No.: 287,407

[22] Filed: Aug. 8, 1994

Related U.S. Application Data

[63] Continuation-in-part of Ser. No. 269,139, Jun. 30, 1994, which is a continuation-in-part of Ser. No. 55,578, May 3, 1993, abandoned.

[51] Int. Cl.$^6$ .................................................. A61B 3/107
[52] U.S. Cl. ............................ 606/4; 606/2; 606/10; 128/774; 33/1 B; 33/262; 33/511; 33/512; 33/533
[58] Field of Search .................................. 128/774–781; 606/1, 34, 10; 33/1 B, 1 E, 262, 297, 511–515, 533, 546

[56] References Cited

U.S. PATENT DOCUMENTS 4,483,075  11/1984  Kundin ........................................ 33/512
5,261,822  11/1993  Hall et al. .

*Primary Examiner*—David M. Shay
*Attorney, Agent, or Firm*—Paul M. Denk

[57] ABSTRACT

A thin, pliable mat to enhance visualization of corneal topography during rastostereography or videokeratoscopy. The mat is approximately 20 microns or less in thickness and constructed from hydrophobic material. In one preferred embodiment, the mat has a pattern etched thereon. In an alternative embodiment, a pattern is projected onto the mat. For rastostereography the pattern is a grid. For videokeratoscopy the pattern is concentric circles. The mat conforms to the surface of the cornea and the pattern is analyzed using conventional technology to determine corneal topography.

7 Claims, 2 Drawing Sheets

1

CORNEAL TOPOGRAPHY ENHANCEMENT DEVICE

CROSS-REFERENCE TO RELATED APPLICATIONS

This application is a continuation-in-part of application entitled Method of Evaluating a Laser Used in Ophthalmological Surgery, Ser. No. 38/269,139, filed Jun. 30, 1994; which is a continuation-in-part of application entitled Method of Calibrating Lasers for Use in Ophthalmological Surgery, Ser. No. 08/055,578, filed May 3, 1993, now abandoned. both applications owned by the same inventor.

BACKGROUND OF THE INVENTION

This invention relates generally to opthalmological surgery devices, more specifically, to a device and method for enhancing the visualization of corneal topography.

In corneal surgery, particularly photorefractive keratectomy (PRK), the surgeon determines the corneal topography to assess the effective corneal ablation. For example, the surgeon can use rastostereography for imaging a corneal surface or ablation test surfaces. A method of using rastostereography to evaluate the effect of a surgical laser on the cornea or test substrate is disclosed in my co-pending application Ser. no. 08/055,578, filed May 3, 1993 which is hereby incorporated by reference. Furthermore, the use of a Placido-disc videokeratoscopy to evaluate a surgical laser is disclosed in my co-pending application Ser. No. 08/269,139, filed Jun. 30, 1994, and entitled Method of Evaluating a Laser Used in Ophthalmological Surgery, also incorporated herein by reference.

In such procedures, a grid or concentric circle image is projected onto the cornea. The image is captured with a video frame-grabber and then analyzed by a computer to determine the topography of the cornea. Such analysis informs the surgeon of the elevations and depressions on the corneal surface. As disclosed in the above referenced applications, the surgeon can use the rastostereography or videokeratoscopy prior to laser ablation of a test substrate and then after ablation to evaluate the effect of the laser on the substrate. Moreover, the surgeon can perform rastostereography or videokeratoscopy procedure on the cornea before and after surgical ablation of the cornea to determine whether or not there are high or low elevations. That is, the topographical analysis will inform the surgeon of any "hot" or "cold" spots on the cornea.

Prior art methods of using rastostereography, for example, are limited by the need to use a fluorescein dye in order to adequately capture the grid projected on the cornea. The use of fluorescein dye can cause inconsistencies and unreliable results. The variable thickness of the liquid dye layer on the surface of the cornea can be a problem. Moreover, corneal surfaces, particularly immediately after ablation, absorb some dye. Absorption causes a variable thickness of the dye layer on the ablated cornea surface. Furthermore, the fluorescein dye can interact with ultra-violet laser energy resulting in inconsistent and unpredictable laser energy absorption and ablation of the tissue, and disrupt the accuracy of the entire surgical procedure.

SUMMARY OF THE INVENTION

It is, therefore, among the principal objects of the present invention to provide a very thin, pliable mat bearing a discrete pattern placed on the corneal surface to enhance topographic visualization.

Another object of the invention is to provide such a mat that conforms to the surface topography of the cornea.

Still another object of the invention is to provide such a mat having a clear or opaque background with a contrasting pattern to enhance visualization of the pattern.

Yet another object of the invention is to provide a thin, pliable, mat onto which a conventional pattern can be projected.

In accordance with the invention, briefly stated, a thin, pliable mat is provided to enhance visualization of corneal topography during rastostereographic or videokeratoscopic procedures. The mat is very thin, being 20 microns or less in thickness. The mat is made from a hydrophobic plastic material, acrylic or silicone. In one embodiment, the mat has a discrete pattern etched thereon. For rastostereography, a grid pattern is used. For Placido-disc procedures, concentric circles are used. In an alternative embodiment the mat is a uniform opaque or fluorescein impregnated material onto which a conventional grid or concentric circles are projected. The mat is applied to the surface to be tested so that no fluid or air is behind the mat. The mat conforms to the surface topography. The pattern is analyzed using conventional technology.

BRIEF DESCRIPTION OF THE PREFERRED EMBODIMENT

Figure 1:
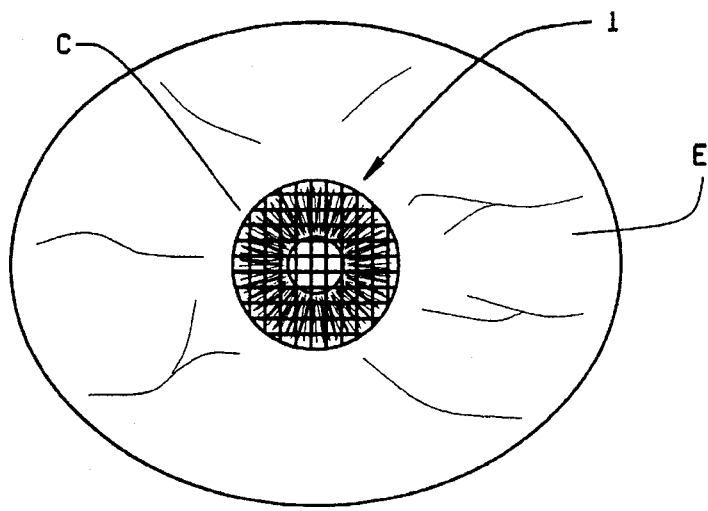
FIG. 1 is a front elevational view of the device for enhancing visualization or corneal topography of the present invention shown applied to the cornea of an eyeball to illustrate environment.
Figure 3:
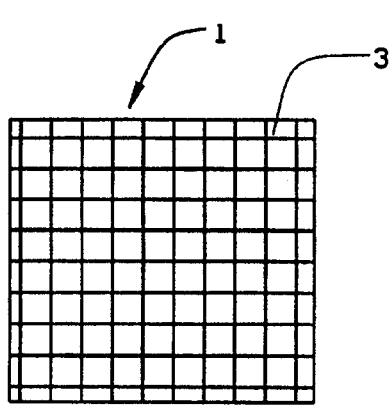
FIG. 3 is an alternative embodiment thereof.

The device for enhancing visualization of corneal topography of the present invention is indicated generally in the Figures by reference numeral 1.

Figure 2:
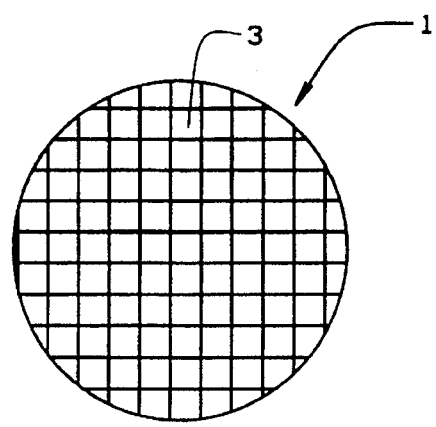
FIG. 2 is top plan of the device for enhancing the visualization of corneal topography of the present invention.

As shown in FIG. 1, device 1 is applied to the cornea C of an eye E. Device 1 is an extremely pliable, small mat approximately 12 mm across. Mat 1 is formed from a very thin, pliable material that conforms to the external physical features of the cornea C of eye E when applied thereto. Mat 1 is constructed from a hydrophobic material that will not absorb moisture from the eye and swell or distort. Mat 1 can be formed from very thin acrylic, silicone or other appropriate polymer material. Mat 1 is preferably approximately 20 microns or less in thickness. Also, in the preferred embodiment, the mat will be approximately 12 mm square or round in configuration. Although shown having a circular or disc-like configuration in FIGS. 1 and 2, mat 1 can be constructed as a square or rectangular as shown in FIGS. 3–8.

Figure 4:
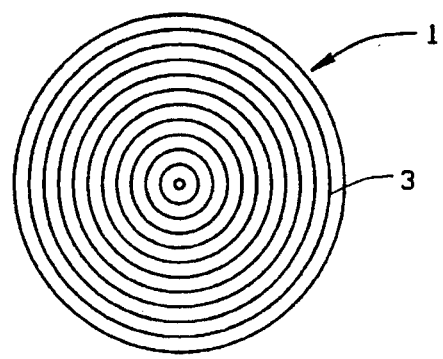
FIG. 4 is an alternative embodiment thereof.

Mat 1 has a discrete pattern 3 on surface S. As shown in FIGS. 1–3 and 5–7, the discrete pattern can be a grid. As shown in FIG. 4 and 8 the discreet pattern is a series of concentric circles. The grid pattern 3 is used in conventional rastostereographic procedures. The concentric circle pattern 3 is used in keratoscopic procedures, particularly Placido-disc keratoscopic procedures. Pattern 3 can be imbedded in mat 3, etched on mat 3, or projected onto surface S of mat 3 as will be described in detail below.

Figure 5:
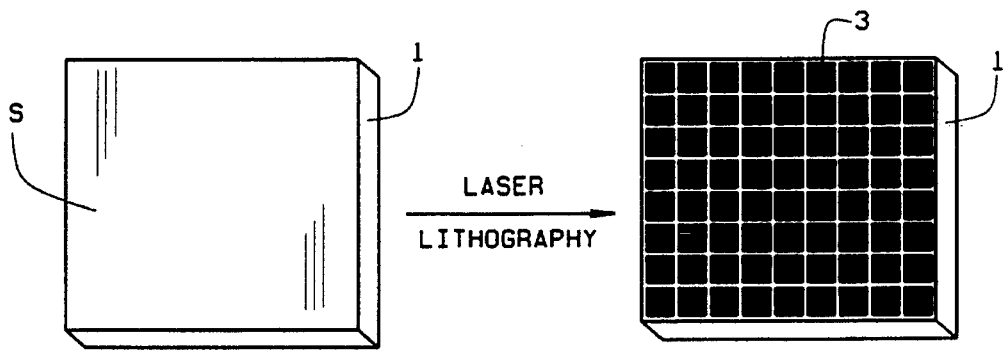
FIG. 5 is a diagrammatic representation of the creation of a pattern on the device for enhancing the visualization of corneal topography of the present invention.

Pattern 3 can be an ink pattern imbedded in mat 3. Preferably, however, pattern 3 is formed by a laser lithographic procedure, as illustrated in FIG. 5. As shown in FIG. 5, mat 1 is a white acrylic material with surface S uniformly black. Laser etching removes the black ink or dye exposing the underlying white background to form a white grid pattern 3. Obviously, the colors can be reversed and the mat can be black and surface S white. Laser etching would reveal a black grid pattern 3.

Figure 6:
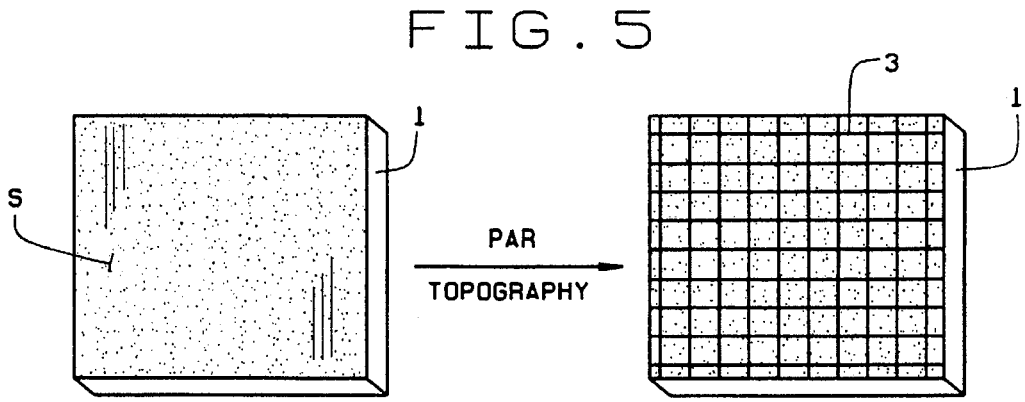
FIG. 6 is an alternative embodiment thereof.

FIG. 6 illustrates another method of forming a pattern on mat 1. Mat 1 is impregnated with fluorescein dye. Pattern 3 is projected onto mat 1 by a conventional topographic system, e.g., as available from PAR Technologies, New Hartford, N.Y. Alternatively, pattern 3 can be a pattern of concentric circles projected onto mat 1 by Placido-disc keratoscopic equipment.

Figure 7:
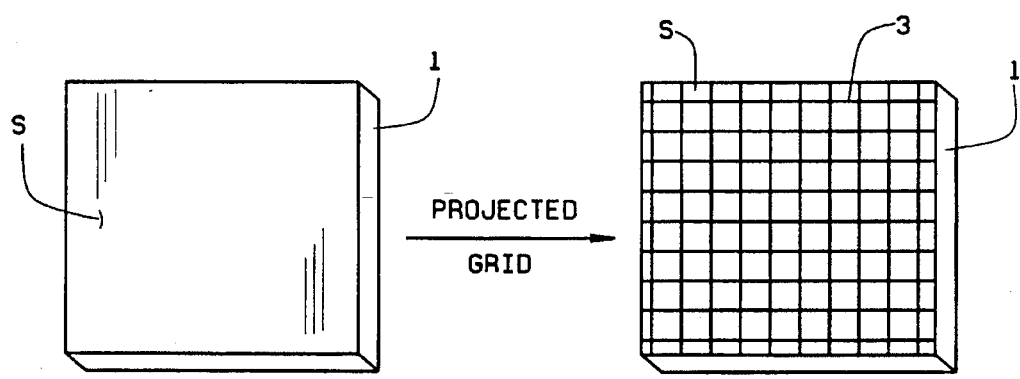
FIG. 7 is another alternative embodiment thereof.
Figure 8:
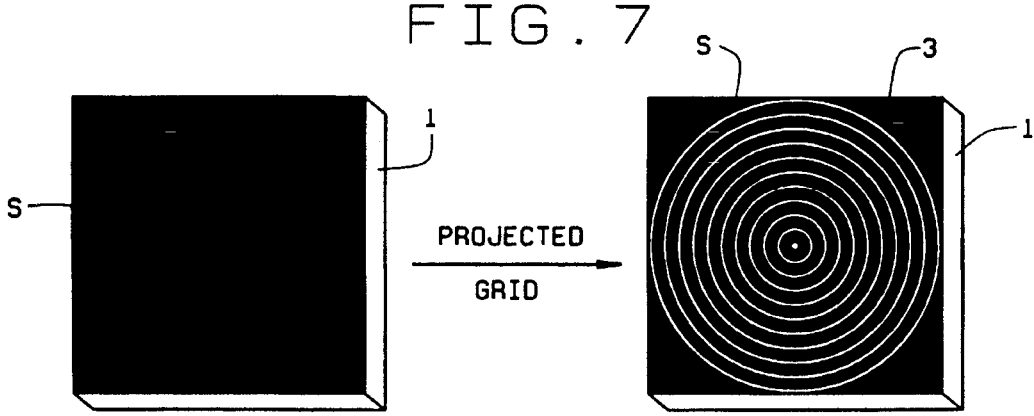
FIG. 8 is still another alternative embodiment thereof.

FIGS. 7 and 8 illustrate another alternative embodiment of mat 1. FIG. 7 shows a white mat 1 with a black pattern 3 projected thereon by conventional rastostereogrammetry equipment. FIG. 8 illustrates a black mat 1 having a pattern 3 of concentric circles projected thereon by Placido-disc videokeratoscopic equipment.

In use, a mat 1 is applied to the cornea of Eye E, as shown in FIG. 1. Mat 1 completely conforms to the surface contours of the cornea. If pattern 3 is distorted when conforming to the surface of cornea C, any fluid or air is expressed from under mat 1 to attain complete contiguity. If mat 1 has a pattern 3 formed thereon, for example by the procedure illustrated in FIG. 5, conventional topographic analysis equipment is used to analyze that pattern and compute a topographical map of the cornea. If there is no pattern on mat 1, a pattern 3 is projected onto the map (FIGS. 6–8) and that pattern is analyzed by conventional techniques. Analysis of a pattern 3 carried by a mat or projected onto mat 3 eliminates the drawbacks associated with projecting a pattern directly onto the naked cornea, or requiring the use of fluorescein, as aforesaid.

It will be appreciated that various changes and modification can be made in the device of the present invention without departing from the scope of the appended claims. Therefore, the foregoing description and accompanying drawings are intended to be illustrative only and should not be construed in a limiting sense.

I claim:

1. A device to be placed on the surface of the cornea to aid in the visualization of the topography of the cornea in preparation for the performance of corrective laser surgery, comprising:

a mat, said mat being thin and pliable and formed of a hydrophobic polymer material so as to not absorb any moisture of the eye, said mat having an outer surface, said mat having a thickness of approximately 20 microns or less, and having a width of approximately 12 millimeters in one of a round and square configuration so as to completely conform to the surface contours of the cornea;

a discrete pattern provided on said outer surface of said mat so that said pattern can reflect the topography and be visualized and analyzed by the laser to determine the precise topography of the entire surface of the cornea before or after cornea surgery.

2. The device of claim 1 wherein said discrete pattern is a grid.

3. The device of claim 1 wherein said discrete pattern is a plurality of concentric circles.

4. The invention of claim 1 wherein said discrete pattern is formed on a surface of said mat.

5. The device of claim 1 wherein said discrete pattern is projected onto a surface of said mat.

6. The device of claim 1 wherein said mat is approximately 12 μm square.

7. The device of claim 1 wherein said mat is approximately 12 μm round.

* * * * *

UNITED STATES PATENT AND TRADEMARK OFFICE
CERTIFICATE OF CORRECTION

PATENT NO. : 5,507,740
DATED : April 16, 1996
INVENTOR(S) : Francis E. O'Donnell, Jr.

It is certified that error appears in the above-indentified patent and that said Letters Patent is hereby corrected as shown below:

Column 4, claim 6, line 39, change "12 um" to ---12 mm---.

Column 4, claim 7, line 41, change "12 um" to ---12 mm---.

Signed and Sealed this

Thirtieth Day of July, 1996

Attest:

BRUCE LEHMAN

*Attesting Officer*    Commissioner of Patents and Trademarks